United States Patent
Clarén et al.

(10) Patent No.: US 6,224,591 B1
(45) Date of Patent: May 1, 2001

(54) DEVICE AND METHOD FOR HYPERTHERMIA TREATMENT

(75) Inventors: Jan Clarén, Lund; Lars Redvall, Göteborg, both of (SE)

(73) Assignee: Atos Medical AB, Horby (SE)

( * ) Notice: Subject to any disclaimer, the term of this patent is extended or adjusted under 35 U.S.C. 154(b) by 0 days.

(21) Appl. No.: 08/922,690

(22) Filed: Sep. 2, 1997

(30) Foreign Application Priority Data

Mar. 1, 1995 (SE) .................................................. 95007589

(51) Int. Cl.[7] .................................................... A61B 18/04
(52) U.S. Cl. ................................ 606/27; 607/96; 607/104; 607/105; 607/113
(58) Field of Search .................................. 606/27, 28, 192, 606/193; 607/96, 100, 101, 104, 105, 113, 114

(56) References Cited

U.S. PATENT DOCUMENTS

| | | |
|---|---|---|
| 2,190,384 | 2/1940 | Newman . |
| 2,734,508 | 2/1956 | Kozinski . |
| 3,369,549 | 2/1968 | Armao . |
| 3,924,628 | 12/1975 | Droegemueller et al. . |
| 4,059,982 | 11/1977 | Bowman . |
| 4,160,455 | 7/1979 | Law . |
| 4,198,981 | 4/1980 | Sinnreich . |
| 4,564,014 | 1/1986 | Fogarty et al. . |
| 4,664,114 | 5/1987 | Ghodsian . |
| 4,676,258 | 6/1987 | Inokuchi et al. . |
| 4,748,979 | 6/1988 | Hershenson . |
| 4,754,752 | 7/1988 | Ginsburg et al. . |
| 4,793,351 | 12/1988 | Landman et al. . |
| 4,796,622 | 1/1989 | Lu et al. . |
| 4,799,479 | 1/1989 | Spears . |
| 4,820,349 | 4/1989 | Saab . |
| 4,823,812 | 4/1989 | Eshel et al. . |
| 4,860,744 | 8/1989 | Johnson et al. . |
| 4,949,718 | 8/1990 | Neuwirth et al. . |
| 4,960,109 | 10/1990 | Lele . |

(List continued on next page.)

FOREIGN PATENT DOCUMENTS

| | | |
|---|---|---|
| 3611971 A1 | 4/1986 | (DE) . |
| 42 33 816 A1 | 4/1993 | (DE) . |
| WO 91/00118 A1 | 1/1991 | (WO) . |
| WO 93/05737 | 4/1993 | (WO) . |
| WO 93/21846 | 11/1993 | (WO) . |

OTHER PUBLICATIONS

Derwent's abstract No. 93–358287/45, week 9345, Abstract of SU 1771725–A1 (Tvetmetavtomatika Urals Branch) Oct. 30, 1992.

Primary Examiner—Linda C. M. Dvorak
Assistant Examiner—David M. Ruddy
(74) Attorney, Agent, or Firm—Merchant & Gould P.C.

(57) ABSTRACT

Device for hyperthermia treatment in a body cavity comprising a catheter (10) to be introduced into the body cavity and being closed at the distal end thereof. An elastically expandable hose piece (18) is mounted at this end, which is sealingly connected to the catheter at both ends of the hose piece. Two passages (11, 12) extend through the catheter and can be connected each to an associated liquid conduit (26, 27) at the proximal end of the catheter. The passages open under the hose piece through side apertures (21, 22) in the catheter so that the hose piece can be expanded as a balloon by the supply of liquid through one passage liquid being drained off through the other passage. The device comprises external means (28, 31) for circulating liquid through the hose piece on the catheter and heating of the circulating liquid. A socket (23) open for fluid flow therethrough at both ends thereof is axially displaceable on the catheter said socket at the distal end thereof forming an abutment to be engaged with cervix when the catheter is introduced into uterus.

11 Claims, 3 Drawing Sheets

U.S. PATENT DOCUMENTS

| | | |
|---|---|---|
| 5,084,044 | 1/1992 | Quint . |
| 5,242,390 * | 9/1993 | Goldrath ................................ 604/55 |
| 5,380,319 | 1/1995 | Saito et al. . |
| 5,449,354 * | 9/1995 | Konwitz et al. ....................... 606/15 |
| 5,449,380 * | 9/1995 | Chin ...................................... 607/105 |
| 5,460,628 * | 10/1995 | Neuwirth et al. ...................... 606/28 |
| 5,645,561 * | 7/1997 | Smith et al. .......................... 606/193 |
| 5,653,692 * | 8/1997 | Masterson et al. ................... 604/113 |
| 5,800,493 * | 9/1998 | Stevens et al. ....................... 607/113 |
| 5,827,269 * | 10/1998 | Saadat .................................... 606/28 |
| 5,827,273 * | 10/1998 | Edwards ................................ 606/41 |
| 5,891,134 * | 4/1999 | Goble et al. ........................... 606/27 |

* cited by examiner

DEVICE AND METHOD FOR HYPERTHERMIA TREATMENT

CROSS REFERENCE TO RELATED APPLICATION

This application is a continuation-in-part of the International Application PCT/SE96/00266 filed Mar. 1, 1996 and mentioning the United States of America as a designated state.

BACKGROUND OF THE INVENTION

1. Field of the Invention

The invention relates to a device for hyperthermia treatment, viz. treatment of body tissues of different kinds under the supply of heat in connection with some deceases.

2. Description of the Related Art

Hyperthermia treatment is described in detail in WO-A-93/05737. This publication describes also a device for hyperthermia treatment in a body cavity, e.g. uterus, comprising a catheter with a distal portion to be introduced into the body cavity. In said distal portion the catheter has an elastic enclosure having an inlet for the supply of pressurized liquid in order to expand said elastic enclosure so that it forms a balloon filling the body cavity. In the catheter there is provided inside the elastic enclosure a heating element for heating the liquid in the balloon by the liquid by means of pressure shocks being circulated in the balloon in heat transferring contact with the heating element. The liquid inlet also serves as an outlet for the liquid when it shall be drained off in order that the elastic enclosure shall contract around the catheter after the treatment having been made. A similar device is described in U.S. Pat. No. 4,949,718.

WO-A-93/21846 discloses a device for hyperthermia treatment which also comprises a member on a catheter to be introduced into a body cavity, said member being expanded in the body cavity by the supply of liquid or gas. In this case the heating is effected by means of electromagnetic waves.

A device for hyperthermia treatment in a body cavity is described also in U.S. Pat. No. 5,084,044 comprising a catheter to be introduced into the body cavity and having two parallel passages to be connected each to an associated liquid conduit in the proximal end of the catheter, and an expandable space defined by an elastically extendable element at the distal end of the catheter said passages opening into said space, means for circulating pressurized liquid through said space via the passages, said element being extended by the liquid as a balloon in the body cavity in engagement with the wall thereof, and external heating means for heating the circulating liquid.

SUMMARY OF THE INVENTION

The invention relates to a device of the kind described in U.S. Pat. No. 5,084,044 for hyperthermia treatment of the endometrium of the uterus, and to a method for such treatment.

One object of the invention is to facilitate the introduction and the correct localization of the catheter in the uterus.

Another object of the invention is to provide a device of the kind referred to which provides protection of the vagina during the treatment.

A further object is to provide a device of the kind referred to which provides for rapid discharge of the pressurized liquid outside vagina if the balloon should rupture during the treatment.

A still further object is to provide a device of the kind referred to which can be easily tested as to the function thereof before the catheter is introduced into the uterus.

It is also an object of the invention to make possible to adjust the size of the balloon to the size of the uterus.

A still another object of the invention is to provide a method allowing supply of pressurized liquid to the catheter at an accurately controlled temperature.

Said objects and additional objects of the invention are achieved by a device for hypertermia treatment of the endometrium of uterus, comprising a catheter to be introduced into uterus and forming two passages to be connected each to an associated liquid conduit in the proximal end of the catheter, an elastically expandable smooth hose piece enclosing the catheter at the distal end thereof said hose piece being sealingly connected to the catheter at both ends thereof to define an expandable space around the catheter said passages opening into said space through side apertures, means for circulating pressurized liquid through said space via the passages to expand said hose piece by the pressurized liquid as a balloon, external heating means for heating the circulating liquid, and a socket open for fluid flow therethrough at both ends thereof which is axially displacable on the catheter said socket at the distal end thereof forming an abutment to be engaged with cervix when the catheter is introduced into uterus.

The invention also provides a method for hyperthermia treatment of the endometrium of uterus, comprising the steps of introducing through vagina and the cervical canal a balloon catheter into uterus, circulating pressurized liquid through the catheter to expand the balloon into engagement with the endometrium, and externally heating the circulating liquid.

In a preferred embodiment of the method a socket open at both ends is provided for axial displacement on said catheter for determining the probe measure and for discharging liquid to a site outside the vagina in case of rupture of the balloon.

Further objects and details of the invention will be apparent from the following description of embodiments of the invention with reference to the accompanying drawings.

DESCRIPTION OF EMBODIMENTS OF THE INVENTION

Figure 1:
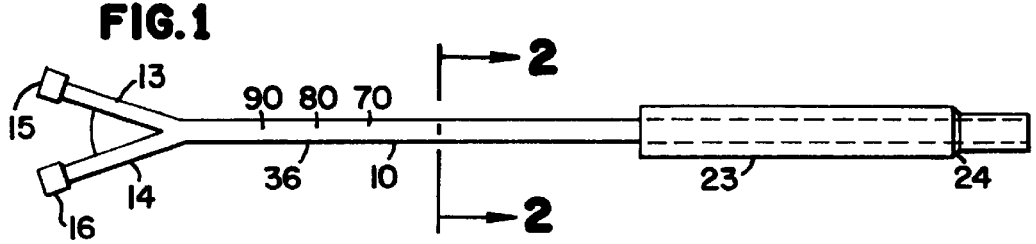
FIG. 1 is a side view of the catheter in a first embodiment of the invention.
Figure 2:
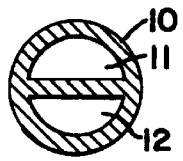
FIG. 2 is an enlarged cross-sectional view along line II—II in FIG. 1.
Figure 3:
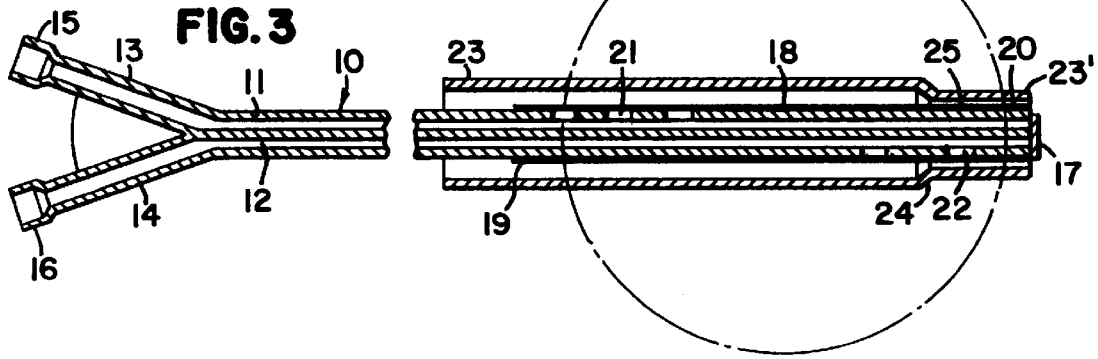
FIG. 3 is an axial cross-sectional view of the catheter in FIG. 1.

The device of the invention in one embodiment thereof comprises a catheter of the construction shown in FIGS. 1 to 3. The catheter comprises a soft tube 10 preferably of plastics, which forms two parallel passages 11 and 12 which are connected at the proximal end of the catheter to a branch conduit 13 and 14, respectively, with a coupling 15 and 16, respectively, for the connection of hoses. Tube 10 is closed at the distal end thereof at 17, and the distal portion of the tube is surrounded by a piece 18 of elastically extendable hose which normally fits against the outside surface of the tube as will be seen from FIG. 3 and is sealingly connected to the tube at the ends of said piece at 19 and 20. The end portion of the catheter 10 to which the hose piece is connected at 20 should be as short as possible. The hose piece has a smooth outside surface and can consist of silicone rubber having a thickness of e.g. 0.3 mm. In the tube wall there are provided apertures 21 adjacent the end 19 of the hose piece, which communicate with passage 11, and apertures 22 adjacent the end 20 of the hose piece, which communicate with passage 12. Hose piece 18 can be expanded by the supply of liquid through passage 11 as indicated by dot-and-dash lines 18' in FIG. 3, and can be brought to contract again around the catheter by the liquid being drained off through passage 12.

A socket 23 is mounted on the outside of tube 10 said socket being axially displaceable on the tube. The socket forms adjacent the distal end thereof an outside conical shoulder 24 and terminates at the distal end in a portion 23' which has a smaller outside diameter than the rest of the socket. The socket has such a length that it can cover completely at least the expandable portion of hose piece 18. Inside the distal end portion of the socket, having reduced diameter there are provided axial ribs 25 separated by axial grooves for a purpose to be described below.

Figure 4:
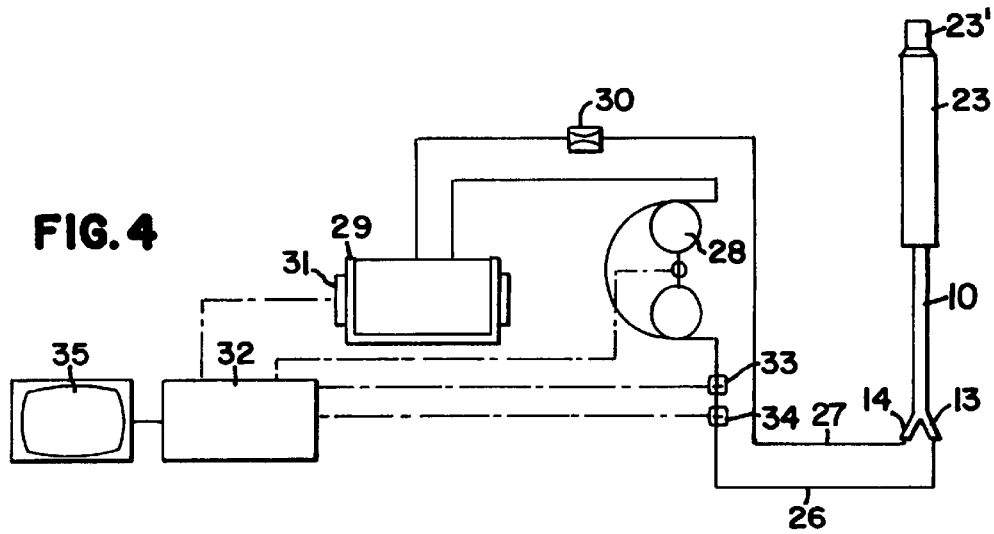
FIG. 4 is a diagrammatic view of the device of the invention.

In FIG. 4 the catheter described is shown with the branch connection 13 connected to a hose 26 and with the branch connection 14 connected to a hose 27. Hose 26 is connected via a peristaltic pump 28 to a liquid tank 29, and hose 27 is connected to said liquid tank via a restriction 30. A heating element 31 is provided on the liquid tank for heating the liquid therein. This heating element can be of the type comprising a flexible strip with heating wires embedded therein and is located on the outside of the tank. The liquid preferably comprises physiological sodium chloride solution in order not to cause damage if the liquid at the hyperthermia treatment due to some incident should enter the body.

Pressurized liquid can be supplied to the hose piece 18 by means of the peristaltic pump 28 via hose 26, branch conduit 13, passage 11 and apertures 21. Liquid can be drained off from the hose piece via apertures 22, passage 12, branch conduit 14, hose 27, and restriction 30 back to tank 29. The pressure of the liquid can be controlled by stepless adjustment of the rotational speed of pump 28.

A computer 32 receives via sensors 33 and 34 on hose 26 signals indicating temperature and pressure of the liquid supplied to passage 11, and is operatively connected to heating element 31 and the drive motor of the peristaltic pump 28, respectively, as indicated by dot-and-dash lines in FIG. 4, to control the heating effect, i.e. the liquid temperature, and the rotational speed of the pump, i.e. the liquid pressure, respectively, so that temperature and pressure are in agreement with values stored in the computer. The computer shall also have a clock circuit by means of which the desired period of treatment can be set, as well as a program for effecting test and treatment cycles at preset values of temperature and pressure and for a preset period of treatment. A test cycle can also be performed in order to control the tightness of catheter 10 and the connection system thereof before the actual treatment is effected.

When the desired treatment values have been set in the computer two test cycles can initially be performed with socket 23 in the position according to FIGS. 1 and 4 said socket limiting the expansion of hose piece 18. On a display 35 connected to computer 32 the treatment parameters can be read. Initially a test cycle at predetermined values is performed said values being stored in the computer. Then, a second test cycle will be performed with the values to be used in the treatment. These values can comprise either pre-programmed values of the parameters for a standard treatment, i.e. the most frequent treatment, or values which have been programmed for the actual treatment and are specific for said treatment. The two test cycles (or more test cycles than two) can be performed without interruption one test cycle automatically passing into the other so that the user experiences the test cycles as a single step. After the test cycles the actual treatment is performed with the values of the parameters which have been set before the treatment.

Figure 5:
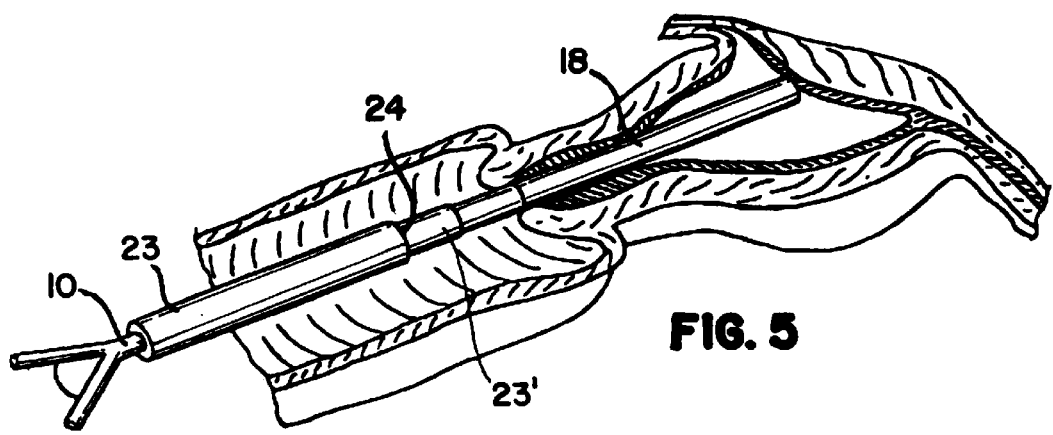
FIGS. 5 to 7 are perspective views illustrating the introduction and use of the catheter in hyperthermia treatment of uterus.
Figure 6:
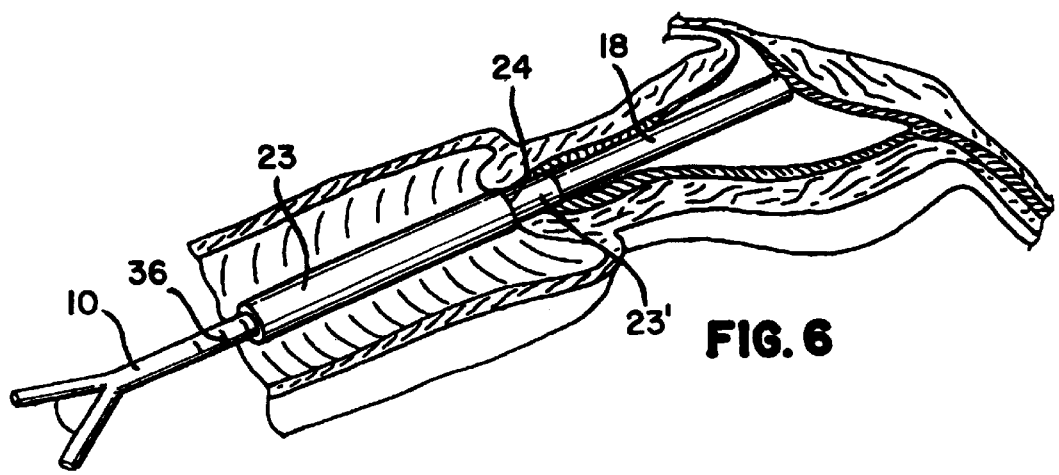
Figure 7:
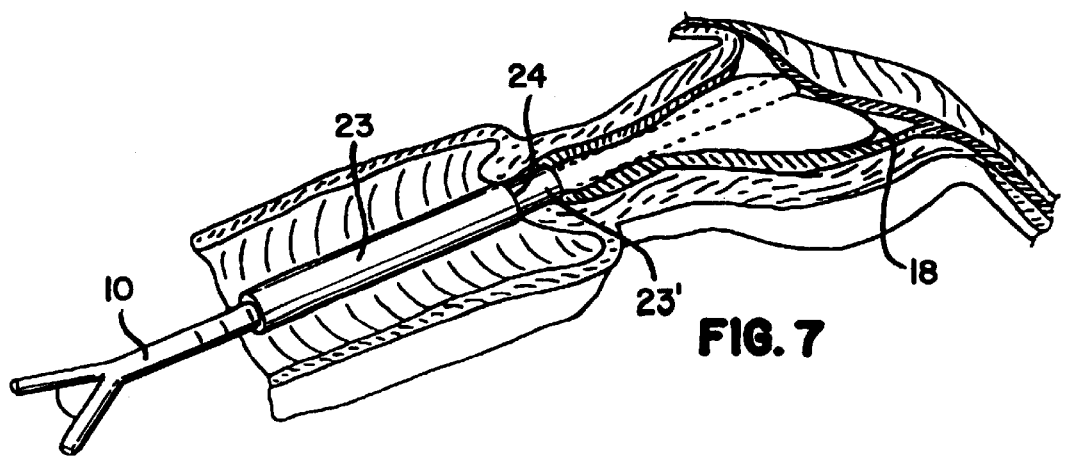

With reference to FIGS. 5 to 7 the introduction and the correct location of the catheter in uterus for treatment of the endometrium thereof will be described.

With socket 23 retracted the catheter is introduced into uterus via vagina according to FIG. 5 so that the distal portion of the catheter will be received in uterus the length of which up to cervix can range from about 7 to 9 cm. Then socket 23 is displaced towards the distal end until shoulder 24 engages cervix (FIG. 6) portion 23' being received in the cervical canal. The position of the socket (the so called probe measure) then preferably can be read at the proximal end of the socket against a scale 36 indicated on tube 10. The expandable portion of hose piece 18 is defined in relation to the length of uterus by the position of socket 23 on the catheter; a major or minor portion of the expandable part of the hose piece is surrounded by socket 23 in dependence of uterus being larger or smaller so that only that portion of the hose piece is brought to expand which can be engaged with the wall of uterus the sensitive cervical duct being protected by socket 23. This also protects the mucous membrane of vagina and the cervical duct against burns during treatment.

Thus, socket 23 the main use of which is in the test cycles in the embodiment can be used also for limiting the expansion of hose piece 18 during treatment so that the balloon formed by said hose piece can be adapted to the size of uterus forming a closed space with an inlet through which the catheter is introduced.

During a treatment cycle controlled by computer 32 heated liquid which is at the previously preset temperature and pressure will now be supplied via passage 11 to hose piece 18 which thus will expand and will be pressed against the wall of uterus for hyperthermia treatment thereof, FIG. 7. The liquid returns through passage 12 via restriction 30 to tank 29 and will be kept in continuous circulation at preset temperature and pressure during treatment. Typical values at the treatment of uterus are about 85° C., an internal liquid pressure of about 200 mm Hg, and about 11 min.

The pressure should be adjusted such that the balloon formed by hose piece 18 has satisfactory contact with the tissue of uterus not only at the site to be treated but also in other areas in order that blood flow from the tissues will be blocked. Particularly at the distal end of the catheter it is essential that the projecting portion at 20 is as short as possible so that the balloon will not be kept out of contact with the wall of uterus over an extended area in that region.

During the treatment the mucous membrane (endometrium) of uterus is heated so that it will get loose and can be removed.

In an emergency situation wherein the balloon ruptures and liquid at high temperature flows into uterus the liquid should be discharged therefrom rapidly in order to avoid burns. Ribs 25 mentioned above maintain a gap between the outside surface of the catheter and the inside surface of socket 23 so that the liquid can flow through that gap from uterus into and through socket 23 in order to be discharged outside vagina.

When the treatment is completed after the preset period pump 28 will be stopped and the liquid will be allowed to return to the tank via passage 12 and restriction 30, hose piece 18 contracting around tube 10. Then, the catheter is removed from uterus.

All steps of the treatment cycles are controlled by the computer.

Catheter 10 with socket 23 can be delivered as a one way product together with hose set 26, 27 in a sterile package for mounting the hose set in a unit comprising pump, restriction, liquid tank, sensors, computer, and display as well as a key set for programming the treatment values and initiating the operational cycles.

Liquid tank 29 can comprise a cuff with a heating element, wherein a standard bag or a container of any other type with physiological sodium chloride solution is located and to which the sterile hose set is connected by means of conventional connection means.

Figure 8:
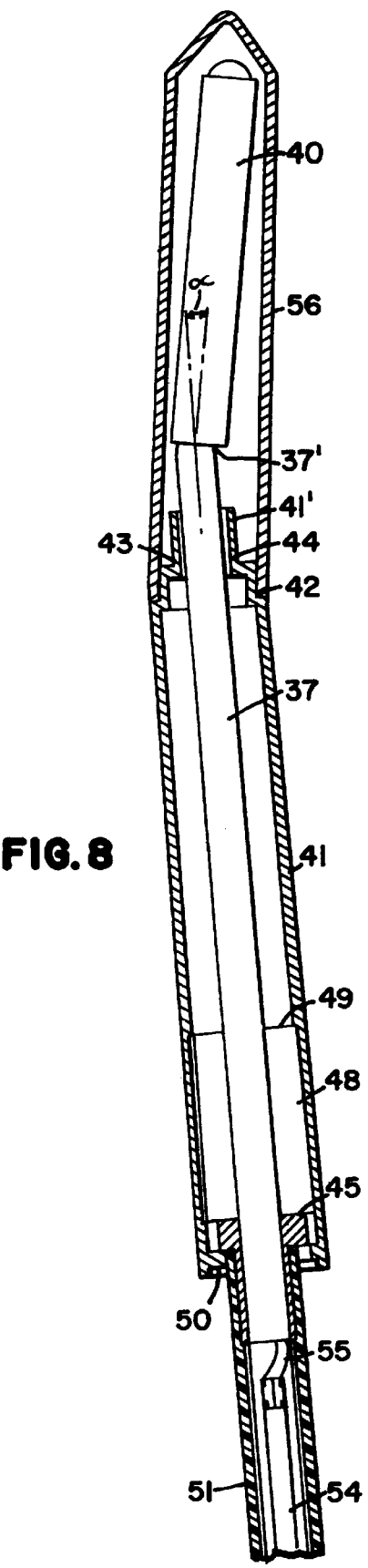
FIG. 8 is an axial cross sectional view of the catheter in a second embodiment of the invention.

FIG. 8 shows the at present preferred embodiment of the device of the invention.

Figure 9:
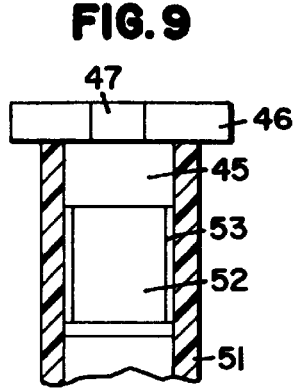
FIG. 9 is an enlarged side view of a detail of the catheter in FIG. 8.
Figure 10:
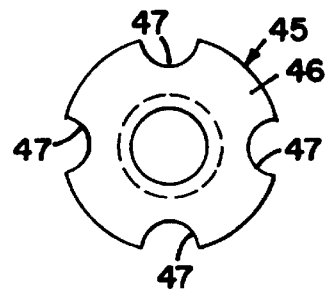
FIG. 10 is an end view of the detail shown in FIG. 9.
Figure 11:
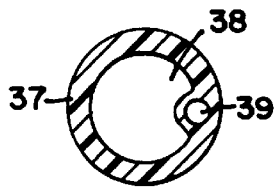
FIG. 11 is an enlarged cross sectional view of the tube forming the catheter.

The catheter in this case comprises a rigid tube 37 preferably of plastics, which in this case, as seen in FIG. 11, forms a primary lumen 38 and a secondary lumen 39. The distal end portion 37' of the catheter tube is angled in relation to the rest of the tube at an angle α in the range of about 10–30°, preferably about 15° in order to facilitate the introduction of the catheter through vagina and the cervical canal into uterus. A piece of elastically extendible hose 40 is provided on the tube portion 37' as previously described in connection with the first embodiment of the invention. A cylindrical socket 41 is provided on the catheter and forms at the distal end a shoulder 42 then a further shoulder 43 to terminate at the distal end in a portion 41' having reduced outside diameter. The tube 37 passes through the portion 41' the inside diameter of which is slightly larger than the outside diameter of the tube so that there is a gap 44 between the outside surface of the tube and the inside surface of portion 41'. At the proximal end of the tube 37 there is fixedly mounted to the tube a sleeve 45 which is shown in the enlarged views of FIGS. 9 and 10. This sleeve forms a radial flange 46 at one end thereof, and in the edge of this flange four equally spaced semi-circular notches 47 are provided. The flange 46 is received in a portion 48 of the socket, which has a slightly increased inside diameter so that there is formed inside the socket a shoulder 49 at the distal end of the portion. At the proximal end of the portion 48 an inside circumferential bead 50 is provided and this bead and the shoulder 49 limit the stroke of axial displacement of the socket 41 on the catheter.

A hose 51 for the supply of pressurized liquid to the expandable space of the catheter is slipped over the sleeve 45 which has a portion 52 of reduced outside diameter so that a space 53 is formed between the sleeve and the hose, in which an adhesive can be received in order to securely connect the hose to the sleeve. A hose 54 of smaller diameter extends inside the hose 51 and is connected to a metal tube 55 which is inserted into the lumen 39 of the tube 37 and communicates the hose 54 with said lumen. The hose 54 is intended for draining off liquid from the expandable space. Apertures communicating lumen 38 and lumen 39, respectively, with the expandable space are provided in this embodiment in the same way as described with reference to FIG. 3.

The shoulder 42 forms an oblique angle with the axis of the socket 41 of the same order as the angle α, and an elongated cylindrical cap 56 enclosing the expandable space is detachably mounted on the reduced distal end portion of the socket 41, engaging the shoulder 42. As will be understood from FIG. 8 the socket 41 cannot be displaced to a position in which it covers the expandable space in this embodiment and therefore the cap 56 is provided for performing a test cycle as described above.

The catheter disclosed in FIG. 8 is used in the same way as described above. When the test cycle has been performed and the cap 56 has been removed the catheter is inserted into uterus through vagina as shown in FIG. 5 in order to place the expandable space in uterus. By axial displacement of the socket 41 the shoulder 43 is engaged with cervix and the narrower distal portion 41' of the socket is introduced into the cervical canal. The treatment is performed as described above.

The socket 41 can be made of translucent or transparent plastics and be provided with a scale, and the sleeve 45 can be made of coloured material (plastics) so that the position thereof will be seen on the scale in order to indicate the probe measure.

In an emergency situation wherein the balloon ruptures the liquid contained therein will flow into the socket 41 through the gap 44 and will be discharged from the socket at the proximal end thereof through the notches 47. Thus, injuries to the endometrium and vagina by contact with the hot liquid will be avoided.

What is claimed is:

1. Device for hyperthermia treatment of the endometrium of a patient's uterus, comprising a catheter to be introduced into the patient's uterus and forming two passages to be connected each to an associated liquid conduit in a proximal end of the catheter, an elastically expandable smooth hose piece enclosing the catheter at a distal end thereof over the total length of the hose piece said hose piece being sealingly connected to the catheter at both ends of the hose piece to define an expandable space around the catheter said passages opening into said space through side apertures, means for circulating pressurized liquid through each space via the passages to expand said hose piece between the connected ends thereof by the pressurized liquid as a balloon, external heating means for heating the circulating liquid, and a socket open for fluid flow therethrough at both ends thereof which is axially displacable on the catheter over the hose piece, said socket at a distal end thereof forming an abutment to be engaged with the patient's cervix when the catheter is introduced into the patient's uterus.

2. Device as in claim 1, wherein the socket forms an outside shoulder adjacent the distal end of the socket, said shoulder providing said abutment.

3. Device as in claim 1, further comprising a scale on the catheter against which the displaced position of the socket on the catheter can be read at a proximal end of the socket.

4. Device as in claim 1, wherein one or more side apertures for one passage are provided adjacent the distal end of the catheter and one or more side apertures for the other passage are provided spaced from said distal end.

5. Device as in claim 1, wherein said socket is dimensioned to surround the expandable space substantially over the total length thereof.

6. Device as in claim 1 further comprising a cap demountably connected to said socket at the distal end thereof and enclosing the expandable space over the total length thereof.

7. Device as in claim 1 wherein a distal end portion of the catheter, around which said expandable space is provided is angled in relation to the rest of the catheter.

8. Device as in claim 7 wherein said portion is angled at an angle of about 10 to 30°.

9. Device as in claim 1 further comprising an outside flange on the catheter, and two inside abutments in the socket at the proximal end thereof said abutments being mutually spaced axially said flange being guided in the socket for axial displacement of the socket between said abutments.

10. Device as in claim 9 wherein said flange forms peripheral notches for fluid flow at the proximal end of the socket.

11. Device for hypothermia treatment of the endometrium of a patient's uterus, comprising a catheter to be introduced into the patient's uterus and forming two passages to be connected each to an associated liquid conduit in a proximal end of the catheter, an elastically expandable smooth hose piece enclosing the catheter at a distal end thereof over the total length of the hose piece said hose piece being sealingly connected to the catheter at both ends of the hose piece to define an expandable space around the catheter said passages opening into said space through side apertures, means for circulating pressurized liquid through each space via the passages to expand said hose piece between the connected ends thereof by the pressurized liquid as a balloon, external heating means for heating the circulating liquid, and a socket open for fluid flow therethrough at both ends thereof which is axially displacable on the catheter over the hose piece, said socket at a distal end thereof forming an abutment to be engaged with the patient's cervix when the catheter is introduced into the patient's uterus, wherein the socket forms an outside shoulder adjacent the distal end of the socket, said shoulder providing said abutment.

* * * * *